(12) United States Patent
Fischer et al.

(10) Patent No.: US 8,772,527 B2
(45) Date of Patent: Jul. 8, 2014

(54) PROCESS FOR ISOMERIZATION OF CIS-2-PENTENENITRILE TO 3-PENTENENITRILES

(71) Applicant: BASF SE, Ludwigshafen (DE)

(72) Inventors: Rolf-Hartmuth Fischer, Heidelberg (DE); Alfred Oftring, Bad Dürkheim (DE); Robert Baumann, Mannheim (DE); Hermann Luyken, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/867,671

(22) Filed: Apr. 22, 2013

(65) Prior Publication Data

US 2013/0289299 A1 Oct. 31, 2013

Related U.S. Application Data

(60) Provisional application No. 61/639,111, filed on Apr. 27, 2012.

(51) Int. Cl.
*C07C 253/30* (2006.01)

(52) U.S. Cl.
CPC .................................. *C07C 253/30* (2013.01)
USPC .......................................... 558/338; 558/355

(58) Field of Classification Search
None
See application file for complete search history.

(56) References Cited

U.S. PATENT DOCUMENTS

| | | |
|---|---|---|
| 2,145,242 A | 1/1939 | Arnold |
| 3,526,654 A | 9/1970 | Hildebrand |
| 3,564,040 A | 2/1971 | Downing et al. |
| 3,733,355 A | 5/1973 | Harris et al. |
| 3,852,325 A | 12/1974 | King |
| 4,203,916 A | 5/1980 | Zengel et al. |
| 4,275,223 A | 6/1981 | Zengel et al. |
| 4,290,970 A | 9/1981 | Merger et al. |
| 4,388,238 A | 6/1983 | Heitkaemper et al. |
| 4,418,211 A | 11/1983 | Zengel et al. |
| 4,439,370 A | 3/1984 | Zengel et al. |
| 4,457,871 A | 7/1984 | Zengel et al. |
| 4,467,114 A | 8/1984 | Zengel et al. |
| 4,486,603 A | 12/1984 | Zengel et al. |
| 4,497,963 A | 2/1985 | Merger et al. |
| 4,596,678 A | 6/1986 | Merger et al. |
| 5,070,202 A | 12/1991 | Herkes |
| 5,786,313 A | 7/1998 | Schneider et al. |
| 5,849,950 A | 12/1998 | Greindl et al. |
| 6,384,263 B1 | 5/2002 | Herkes |
| 7,361,778 B2 * | 4/2008 | Bartsch et al. ................ 558/462 |
| 7,557,242 B2 | 7/2009 | Kohlstruk et al. |
| 7,566,800 B2 * | 7/2009 | Scheidel et al. ............. 558/355 |
| 7,612,224 B2 * | 11/2009 | Scheidel et al. ............. 558/355 |
| 7,816,551 B2 | 10/2010 | Jungkamp et al. |
| 8,026,387 B2 | 9/2011 | Kloetzer et al. |
| 8,530,690 B2 * | 9/2013 | Luyken et al. ................ 558/462 |
| 2005/0250960 A1 | 11/2005 | Kohlstruk et al. |
| 2010/0274046 A1 | 10/2010 | Kloetzer et al. |
| 2011/0207961 A1 | 8/2011 | Geissler et al. |
| 2012/0248370 A1 | 10/2012 | Oftring et al. |
| 2013/0006013 A1 | 1/2013 | Mattke et al. |

FOREIGN PATENT DOCUMENTS

| | | |
|---|---|---|
| DE | 2027972 A1 | 4/1971 |
| DE | 2710595 A1 | 9/1978 |
| DE | 4319935 A1 | 12/1994 |
| DE | 10323803 A1 | 11/2004 |
| EP | 0018588 A1 | 11/1980 |
| EP | 0027952 A1 | 5/1981 |
| EP | 0028338 A2 | 5/1981 |
| EP | 0126299 A1 | 11/1984 |
| EP | 0566925 A2 | 10/1993 |
| EP | 0745582 A2 | 12/1996 |
| EP | 1191018 A1 | 3/2002 |
| EP | 1593669 A1 | 11/2005 |
| GB | 1284635 A | 8/1972 |
| JP | S62246547 | 10/1987 |
| JP | 2005320334 A | 11/2005 |
| WO | WO-94/29421 A1 | 12/1994 |
| WO | WO-98/54129 A1 | 12/1998 |
| WO | WO-2005/073172 A1 | 8/2005 |
| WO | WO-2005/073176 A1 | 8/2005 |
| WO | WO-2005/073177 A1 | 8/2005 |
| WO | WO-2007/082818 A1 | 7/2007 |
| WO | WO-2011/015541 A1 | 2/2011 |
| WO | WO-2011/042836 A1 | 4/2011 |
| WO | WO-2011/124610 | 10/2011 |
| WO | WO-2012/136474 A1 | 10/2012 |

OTHER PUBLICATIONS

U.S. Appl. No. 61/529,314.
W. von E. Doering et al., "CryptoCope Rearrangement of 1,3-Dicyano-5-phenyl-4,4-d2-hexa-2,5-diene. Chameleonic or Centaruic?" J. Am. Chem. Soc. 1999, 121, 10967-75.

* cited by examiner

*Primary Examiner* — Michael Barker
*Assistant Examiner* — Po-Chih Chen
(74) *Attorney, Agent, or Firm* — Drinker Biddle & Reath LLP

(57) ABSTRACT

The present invention relates to an improved process for batchwise or continuous isomerization of cis-2-pentenenitrile to 3-pentenenitriles in the presence of 1,4-diazabicyclo[2.2.2]octane as catalyst.

6 Claims, 1 Drawing Sheet

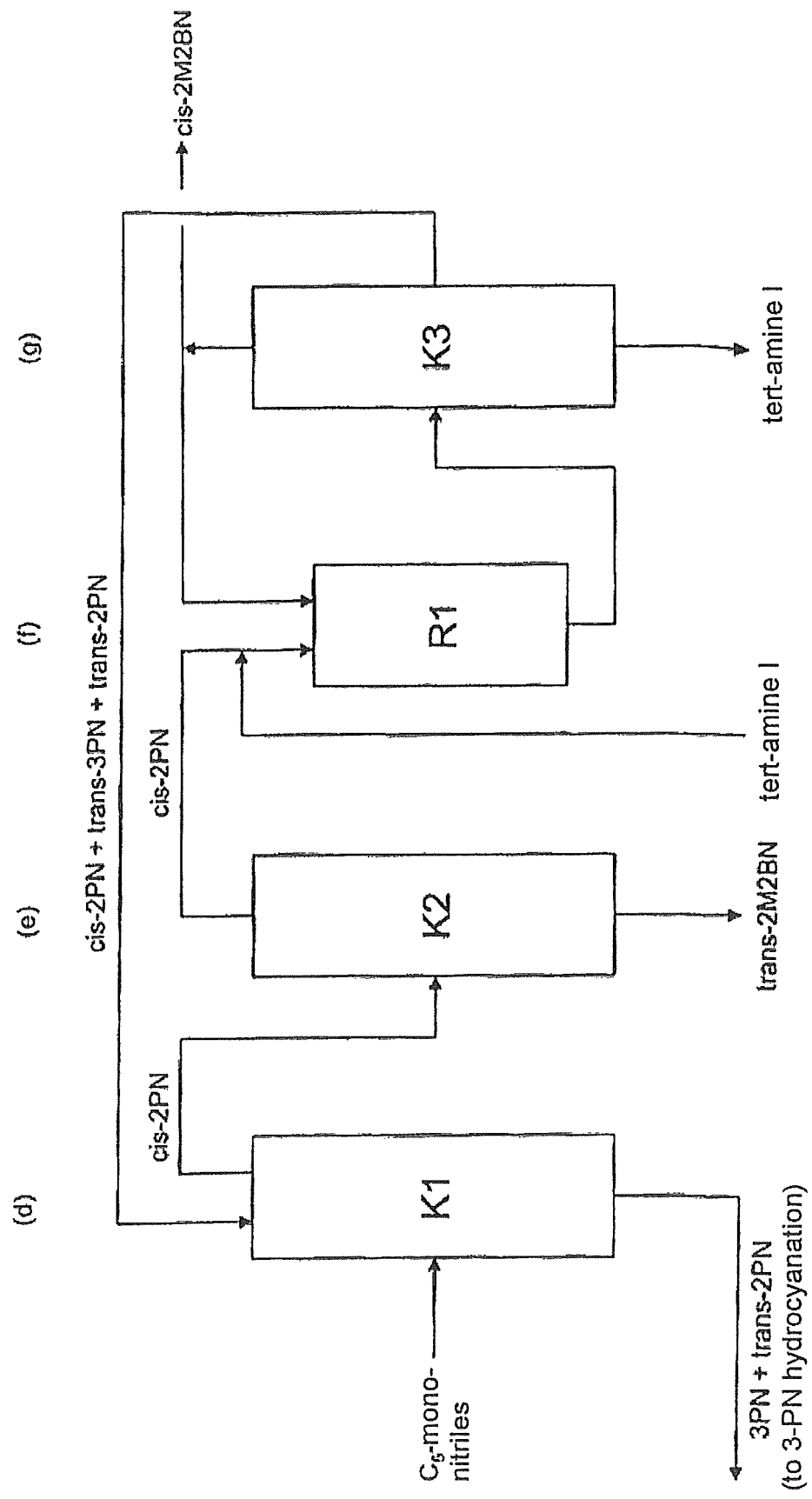

PROCESS FOR ISOMERIZATION OF CIS-2-PENTENENITRILE TO 3-PENTENENITRILES

CROSS-REFERENCE TO RELATED APPLICATIONS

This application claims benefit (under 35 USC 119(e)) of U.S. Provisional Application 61/639,111, filed Apr. 27, 2012, which is incorporated by reference,

BACKGROUND OF THE INVENTION

The present invention relates to an improved process for batchwise or continuous isomerization of cis-2-pentenenitrile to 3-pentenenitriles in the presence of tertiary amines of the formula I as catalysts.

WO-A-05/73176 discloses isomerizing cis-2-pentenenitrile to 3-pentenenitriles with the aid of homogeneously dissolved amines as catalysts, selected from the group of $C_1$- to $C_{20}$-mono- and -diamines.

U.S. Pat. No. 5,070,202 discloses that cis-2-pentenenitrile forms Michael adducts with primary and secondary amines at temperatures of 20 to 200° C.

A disadvantage of these isomerizations is that Michael adducts form from cis-2-pentenenitrile and the amines mentioned as catalysts.

WO 2011/124610 also already discloses using tertiary amines as catalysts for the isomerization of cis-2-pentenenitrile to 3-pentenenitriles. WO 2011/124610 teaches that the use of triethylamine as a catalyst amounts to a conversion of cis-2-pentenenitrile to 3-pentenenitriles of only 13%.

BRIEF SUMMARY OF THE INVENTION

The object was that of providing catalysts which can help to achieve higher yields of 3-pentenenitriles with simultaneously high 3-pentenenitrile selectivities.

An improved process has been developed for isomerization of cis-2-pentenenitrile to 3-pentenenitriles, wherein cis-2-pentenenitrile is isomerized with 1,4-diazabicyclo[2.2.2]octane.

Another object of the invention, therefore, is a process, wherein the catalyst used is 1,4-diazabicyclo[2.2.2]octane.

A BRIEF DESCRIPTION OF THE FIGURE

FIG. 1 depicts an exemplary apparatus that can be used according to the process of the invention.

A DETAILED DESCRIPTION OF THE INVENTION 1,4-diazabicyclo[2.2.2]octane is also denominated as DABCO. In the process according to the invention DABCO can be used alone or mixed with a further tertiary amine. Suitable further tertiary amines are for example those of formula I.

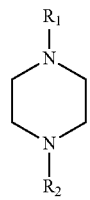

Formula I

In formula I, $R_1$ and $R_2$ may be the same or different. $R_1$ and/or $R_2$ may be chosen from hydrogen, linear and/or branched alkyl radicals having from one to five carbon atoms, cycloalkyl radicals having from five to seven carbon atoms and/or hydroxyethyl radicals. Preferable is a tertiary amine of the formula I in which only one of the $R_1$ and $R_2$ radicals is a hydrogen atom. The process according to the invention can be performed as follows:

cis-2-Pentenenitrile can be isomerized with a tertiary amine of the formula I as a catalyst at temperatures of 80 to 200° C., preferably 90 to 150° C., more preferably 100 to 150° C.

The pressure selected may be from 0.01 to 50 bar, preferably from 0.1 to 30 bar, more preferably from 0.5 to 20 bar, especially standard pressure (atmospheric pressure).

The isomerization can be performed in batchwise or continuous mode. Preference is given to performing the isomerization continuously.

The isomerization of cis-2-pentenenitrile (boiling point 127° C./1013 mbar) gives rise to the target products trans-3-pentenenitrile (boiling point 143° C./1013 mbar) and cis-3-pentenenitrile (boiling point 146° C./1013 mbar), and also small amounts of 4-pentenenitrile (boiling point 146° C./1013 mbar) and trans-2-pentenenitrile (boiling point 144° C./1013 mbar). Trans-3-pentenenitrile, cis-3-pentenenitrile and 4-pentenenitrile can be used, after distillative removal, for the hydrocyanation with hydrogen cyanide to give adiponitrile. cis- and trans-2-pentenenitrile can be recycled into the isomerization stage after distillative removal.

The tertiary amines of the formula I are preferably selected such that the boiling point thereof is higher than the boiling point of cis-3-pentenenitrile. More particularly, the tertiary amines of the formula I so are selected such that the boiling point thereof is from 1 to 100° C., preferably from 2 to 50° C. and more preferably from 3 to 30° C. higher than the boiling point of cis-3-pentenenitrile.

The molar ratio of the tertiary amines of the formula I to cis-2-pentenenitrile can be varied within wide limits and is generally from 0.1:1 to 1:1 mol, preferably from 0.1:1 to 0.5:1, more preferably from 0.15:1 to 0.3:1 mol.

The reaction output from the isomerization can be worked up by distillation. Unconverted cis-2-pentenenitrile can be removed as a top product and recycled. trans-3- and cis-3-pentenenitrile can, after removal and recycling of catalysts having higher boiling points than cis-3-pentenenitrile, be used for pentenenitrile hydrocyanation.

Suitable cis-2-pentenenitrile is pure cis-2-pentenenitrile, mixtures comprising cis-2-pentenenitrile or by-product streams from the hydrocyanation of 1,3-butadiene which comprise cis-2-pentenenitrile, preferably more than 50% by weight of cis-2-pentenenitrile, more preferably more than 70% by weight of cis-2-pentenenitrile.

Suitable catalysts for the isomerization are tertiary amines of the formula I or mixtures thereof. The catalysts are also referred to hereinafter as nitrogen bases.

Suitable tertiary amines of the formula I are, for example, N-methyl piperazine, N-ethylpiperazine, n-propylpiperazine, N-i-propylpiperazine, N-n-butylpiperazine, N-i-butyl-piperazine, N-sec-butylpiperazine, N-tert-butylpiperazine, N,N-dimethylpiperazine, N,N-diethylpiperazine, N-methyl-N-ethylpiperazine, N,N-di-n-propylpiperazine, N,N-di-i-propylpiperazine, N,N-di-n-butylpiperazine, N,N-di-i-butylpiperazine, N,N-di-sec-butylpiperazine, N,N-di-tert-butylpiperazine, N-ethyl-N-cyclohexylpiperazine, N-hydroxyethylpiperazine, or mixtures of these amines of the formula I.

1,4-diazabicyclo[2.2.2]octane (DABCO) (boiling point 174° C./1013 mbar) can be prepared, for example, by heating N-hydroxyethylpiperazine.

cis-2-Pentenenitrile, the starting material for the isomerization to 3-pentenenitriles, forms, for example, in the hydrocyanation of 3-pentenenitriles to adiponitrile.

The two-stage preparation of adiponitrile proceeding from butadiene and hydrogen cyanide is known (Hans-Jürgen Arpe, Industrielle Organische Chemie [Industrial Organic Chemistry], 6th edition 2007, Wiley-VCH publishers, pages 272 to 273).

In the first reaction step, butadiene is hydrocyanated in liquid phase in the presence of nickel(0)-tritolyl phosphite complexes as catalysts. A mixture of isomeric pentenenitriles and methylbutenenitriles is isolated, especially 3-pentenenitriles and 2-methyl-3-butenenitrile. 2-Methyl-3-butenenitrile is isomerized to 3-pentenenitriles.

In the second reaction step, 3-pentenenitrile is hydrocyanated with hydrogen cyanide in liquid phase. The step is conducted in the presence of the same nickel(0)-tritolyl phosphite complexes, to which a Lewis acid, such as zinc chloride, is added.

Adiponitrile, further dinitriles and the nickel(0) catalyst complex are removed from the hydrocyanation output. Optionally after regeneration, the catalyst is recycled into the hydrocyanation.

The organic phase obtained in the workup comprises essentially unsaturated $C_5$-mononitriles selected from the group of cis-2-pentenenitrile, trans-3-pentenenitrile, cis-3-pentenenitrile, 4-pentenenitrile, trans-2-pentenenitrile, cis-2-methyl-2-butenenitrile, trans-2-methyl-2-butenenitrile, 2-methyl-3-butenenitrile.

This $C_5$-mononitrile stream may comprise 0.1 to 10% by weight of cis-2-pentenenitrile, especially 1 to 5% by weight of cis-2-pentenenitrile.

For batchwise isomerization, a cis-2-pentenenitrile obtained in this way can first be removed by distillation from the $C_5$-mononitrile mixture. For the isomerization, a cis-2-pentenenitrile with a purity of greater than 50%, preferably greater than 70%, can be used, the percentages by weight relating to the sum of all components of the mixture.

In a particularly preferred embodiment, the isomerization can be performed continuously in integrated mode with DABCO having a higher boiling point compared to cis-2-pentenenitrile as catalyst. Integrated mode is understood to mean that cis-2-pentenenitrile, mixtures of 3-pentenenitrile and trans-2-pentenenitrile and the DABCO are recycled continuously into the particular process stages, which means that all recycle streams are in operation.

A continuous integrated process for isomerization of cis-2-pentenenitrile to 3-pentenenitriles may comprise the following steps:
a) 3-pentenenitriles or a mixture comprising 3-pentenenitriles is/are hydrocyanated to adiponitrile in the presence of nickel(0)-phosphorus ligand complexes as catalysts,
b) adiponitrile, 2-methylglutaronitrile and nickel(0)-phosphorus ligand complex are removed from the hydrocyanation output,
c) the cis-2-pentenenitrile in the thus obtained organic phase comprising essentially unsaturated C5 mononitriles such as cis- and trans-3-pentenenitriles, 4-pentenenitrile, trans-2-pentenenitrile, cis-2-methyl-2-butenenitrile, trans-2-methyl-2-butenenitrile, 2-methyl-3-butenenitrile is isomerized to 3-pentenenitriles with the aid of DABCO as a catalyst which has a higher boiling point at standard pressure than cis-2-pentenenitrile,
wherein
d) the organic phase which comprises essentially unsaturated C5 mononitriles and is obtained in c) is supplied to a distillation column K1. The distillation column K1 may have from 20 to 40 theoretical plates. The distillation column K1 can be operated at a bottom temperature in the range from 70 to 145° C. The distillation column K1 can be operated at a pressure of 100 to 1000 mbar. cis-2-Pentenenitrile and cis- and trans-2-methyl-2-butenenitrile are removed from the distillation column K1 via the top. 3-Pentenenitrile and trans-2-pentenenitrile can be removed via the bottom and recycled into the reaction step for hydrocyanation of 3-pentenenitriles (step a)).

In one embodiment, 3-pentenenitriles and trans-2-pentenenitrile can be drawn off in a side draw and recycled into step a). In one embodiment, high boilers can be discharged as bottom products.
e) The top product from column K1 is fed to a distillation column K2. Column K2 may have from 20 to 40 theoretical plates. Column K2 can be operated at a bottom temperature in the range from 60 to 140° C. Column K2 can be operated at a pressure of 50 to 100 mbar. The top product of column K2 comprises cis-2-pentenenitrile and cis-2-methyl-2-butenenitrile. The bottom product removed and discharged from column K2 is trans-2-methyl-2-butenenitrile. Also supplied to column K2 is a sufficient amount of DABCO and optionally the tertiary amine I respectively, to balance out amine losses in the circuit which arise from discharge.
f) The top product from column K2 and DABCO and optionally the tertiary amine I respectively having a higher boiling point than cis-2-pentenenitrile are supplied to a reactor R1. The reaction product from reactor R1 and DABCO and optionally the tertiary amine I respectively, having a higher boiling point than cis-2-pentenenitrile are supplied to a distillation column K3.
g) The reaction output from reactor R1, which comprises 3-pentenenitriles as isomerization products, trans-2-pentenenitrile, cis-2-methyl-2-butenenitrile, unconverted cis-2-pentenenitrile and DABCO and optionally the tertiary amine I respectively is supplied to a column K3. Column K3 may comprise from 10 to 20 theoretical plates. Column K3 can be operated at a bottom temperature in the range from 100 to 150° C. Column K3 can be operated at a pressure of 100 to 1000 mbar.

The top product from column K3 is recycled into reactor R1. A substream of the top product is discharged in order to prevent accumulation of cis-2-methyl-2-butenenitrile. From a side draw, a stream comprising as well as predominantly cis-2-pentenenitrile, trans-3-pentenenitrile, trans-2-methyl-2-butenenitrile is withdrawn. This stream is recycled to column K1. The bottom product discharged is DABCO and optionally the tertiary amine I respectively with or without high boilers. The DABCO and optionally the tertiary amine I respectively can be recycled into the reactor, optionally after removal of the high boilers, for example in a column or a thin-film evaporator.

In a preferred embodiment of the invention, the reactor R1 is replaced by a reaction column. WO-A-05/73177 describes reaction columns for the isomerization of cis-2-pentenenitrile to 3-pentenenitriles in the presence of homogeneous and heterogeneous catalysts.

The continuous isomerization of cis-2-pentenenitrile to 3-pentenenitriles using DABCO and optionally the tertiary amine I respectively, having higher boiling points than cis-2-pentenenitrile can be performed in apparatus known to those skilled in the art. Suitable apparatus for the distillation is as described, for example, in: Kirk-Othmer, Encyclopedia of Chemical Technology, 4th ed., vol. 8, John Wiley & Sons, New York, 1996, pages 334 to 338, such as sieve tray columns, bubble-cap tray columns, columns with structured packing, columns with random packing, which may also be operated as dividing wall columns. This distillation apparatus is in each case equipped with suitable apparatus for evaporation, such as falling-film evaporators, thin-film evaporators, multiphase helical tubular evaporators, natural circulation evaporators, or forced circulation flash evaporators, and with apparatus for condensation of the vapor stream. The distillation can be performed in a plurality of, such as two or three, apparatuses. The distillation can additionally be effected in one stage in the manner of a partial evaporation of the feed stream.

Useful apparatus for the isomerization is thus customary apparatus as described, for example, in: Kirk-Othmer, Encyclopedia of Chemical Technology, 4th ed., vol. 20, John Wiley & Sons, New York, 1996, pages 1040 to 1055, such as stirred tank reactors, loop reactors, gas circulation reactors, bubble column reactors or tubular reactors, preferably tubular reactors, in each case optionally with apparatus for heat transfer. The reaction can be performed in a plurality of, such as two or three, apparatuses.

For the isomerization, particular preference is given to a stirred tank cascade with 2 to 4, especially 3, stirred tanks, or a flow tube.

The isomerization reactor is operated at temperatures of 100 to 150° C., preferably 100 to 130° C., and pressures of 1 to 20 bar. The residence times in the reactor are 0.5 to 5 hours, preferably 1 to 3 hours. The cis-2-pentenenitrile conversion is 5 to 30%, preferably 10 to 25% and more preferably 10 to 20%.

The process according to the invention for the isomerization is preferably performed in a distillation column at least comprising a bottom zone, a reaction zone and a top zone. The bottom zone, reaction zone and top zone are preferably arranged in the sequence stated from the bottom upward in the distillation column. It is not ruled out that reaction also takes place in the bottom or top zone.

In addition, the distillation column may comprise internals with distillative separating action. These additional internals are preferably arranged below and/or above the reaction zone. In the lower separation zone, i.e. the separation zone below the reaction zone, the high-boiling isomerization product is substantially removed from low-boiling components. For example, trans-2-pentenenitrile and trans-3-pentenenitrile are separated from unconverted cis-2-pentenenitrile. In the upper separation zone, i.e. the separation zone above the reaction zone, low-boiling secondary components are substantially removed from high-boiling components. For example, any trans-2-methyl-2-butenenitrile introduced with the reactant stream is separated here from trans-3-pentenenitrile and trans-2-pentenenitrile. It is equally possible to deplete trans-3-pentenenitrile and trans-2-pentenenitrile from unisomerized cis-2-pentenenitrile. These separations are listed merely by way of example and are not restrictive.

In the case of an optimal column configuration, all of the cis-2-pentenenitrile in the reactant stream can thus be converted without an additional reactor, and all of the trans-3-pentenenitrile can be obtained in the bottoms without an additional separating apparatus. The additional internals with distillative separating action (separation zones) are generally advantageous, but not absolutely necessary. For instance, one of the two or both separation zones may also be dispensed with.

The reaction zone consists generally of a plurality of different component regions with different functions. The component regions differ by the task of transporting gas to the top of the column and the task of directing liquid in the direction of the column bottom. In addition, liquid distributors may be needed within the reaction zone in order to ensure optimal distribution of liquid over the column cross section. Internals for introducing heat into the column may also be present in the reaction zone.

EXAMPLES

Example 1

Isomerization of cis-2-pentenenitrile with 1,4-diazabicyclo[2.2.2]octane (DABCO) as catalyst The $C_5$-mononitrile mixture used as the feedstock was prepared according to WO-A-05/73172, example 1, by hydrocyanating 3-pentenenitrile in the presence of Ni(0) complexes, which had been synthesized proceeding from a ligand mixture of 60 mol % of tri(m/p-tolyl) phosphite and 40 mol % of the chelate phosphonite 1, and zinc chloride. After removal of adiponitrile, further dinitriles and the Ni(0) catalyst, a $C_5$-nitrile mixture was obtained, which comprised, in addition to trans-3-pentenenitrile (trans-3PN), cis-3-pentenenitrile (cis-3PN) and 4-pentenenitrile (4PN), also cis-2-methyl-2-butenenitrile (cis-2M2BN) (5%), trans-2-methyl-2-butenenitrile (trans-2M2BN) (2%), cis-2-pentenenitrile (cis-2PN) (5%) and trans-2-pentenenitrile (trans-2PN). The percentages are based on the sum of all unsaturated nitriles mentioned.

Chelate Phosphonite 1

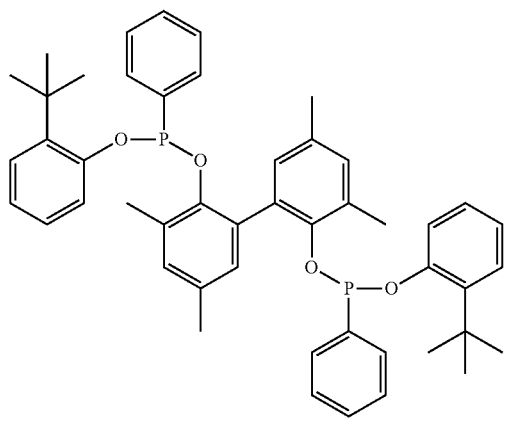

1

The $C_5$ mixture was fed to a column K1 which had 30 theoretical plates and was operated at a bottom temperature of 79° C. and a pressure of 100 mbar. cis-2-Pentenenitrile and cis- and trans-2-methyl-2-butenenitrile distilled over. The bottom products drawn off were 3-pentenenitrile and trans-2-pentenenitrile, which were recycled into step a), the hydrocyanation of 3-pentenenitrile.

The top product of column K1, which comprised 79% by weight of cis-2-pentenenitrile and 10% by weight of 2-methyl-2-butenenitriles, was fed to column 2, which possessed 33 theoretical plates and was operated at a bottom temperature of 72° C. and a pressure of 100 mbar.

The top product of column K2 comprised 86% by weight of cis-2-pentenenitrile and 3% by weight of trans-2-methyl-2-butenenitrile. The bottom product discharged from column K2 was a stream which comprised 61% by weight of trans-2-methyl-2-butenenitrile.

The top product from column K2 was fed to a reactor system R-1 which consisted of a cascade of three stirred tanks. In R-1, the predominant portion of the cis-2-pentenenitrile isomerization took place at a residence time of 4 hours. Catalyst losses, for example as a result of discharge, were compensated for by means of a 1,4-diazabicyclo[2.2.2]octane feed. The isomerization temperature was 125° C., the pressure 2 bar. The molar ratio of cis-2-pentenenitrile to 1,4-diazabicyclo[2.2.2]octane was 1:0.5.

The reaction output from reactor system R-1 was fed to a column K3 which had 15 theoretical plates and was operated at a bottom temperature of 110° C. and a pressure of 250 mbar.

The top product from column K3 was recycled into the reactor system. A substream of the top product (approx. 5% by weight), which comprised cis-2-methyl-2-butene (cis-2M2BN) and cis-2-pentenenitrile, was discharged. A side draw product which consisted to an extent of 79% by weight of cis-2-pentenenitrile was recycled to column K1. DABCO and any high boilers were discharged via the bottom. The DABCO was recycled into reactor R1 after removal of the high boilers.

Example 2

Isomerization of cis-2-pentenenitrile (cis-2PN) to cis- and trans-3-pentenenitrile (cis-+trans-3PN) in the presence of 1,4-diazabicyclo[2.2.2]octane (DABCO) as catalyst A nitrogen-inertized 100 ml flask was charged with 16.2 g (0.2 mol) of cis-2-PN (99.6% pure) and heated to 120° C., and DABCO (0.04 mol) was added while stirring. The reaction mixture was stirred at 119 to 121° C. for 6 hours. After 2, 4 and 6 hours, samples were taken and analyzed by gas chromatography (GC column: 30 m ZB 50, 25 μl, first 11 minutes isothermal at 40° C., then temperature program to 280° C., 10° C. per minute).

Table 1 shows GC area percentages for cis-+trans-2-PN and cis-+trans-3-PN+4-pentenenitrile (4-PN), based in each case on the total GC area for all five linear pentenenitrile isomers.

| | | GC area % | |
|---|---|---|---|
| tert-Amine | Reaction time [h] | cis- + trans 2-PN | cis- + trans 3-PN + 4-PN |
| DABCO | 2 | 55.0 | 45.0 |
| | 4 | 44.9 | 55.1 |
| | 6 | 39.4 | 60.6 |

Example 2 shows that only 55% of the cis-2-pentenenitrile, which was present at the beginning of the reaction in the reaction mixture, is left after a reaction time of 2 hours. After a reaction time of 2 hours, moreover, 45% of the cis-2-pentenenitrile, which was present at the beginning of the reaction, is converted to the target products. If a catalyst according to the WO 2011/124610 (tri-ethylamine) is used, after a reaction time of 2 hours only 13% conversion of cis-2-pentenenitrile are reached.

The invention claimed is:

1. A process for batchwise or continuous isomerization of cis-2-pentenenitrile to 3-pentenenitriles, which comprises isomerizing cis-2-pentenenitrile with 1,4-diazabicyclo[2.2.2]octane.

2. The process according to claim 1, wherein cis-2-pentenenitrile is isomerized at temperatures of 80 to 200° C. and a pressure of 0.01 to 50 bar.

3. The process according to claim 1, wherein the isomerization of cis-2-pentenenitrile to 3-pentenenitriles is performed in a reaction column.

4. The process according to claim 1, wherein
   a) 3-pentenenitriles or a mixture comprising 3-pentenenitriles is/are hydrocyanated to adiponitrile in the presence of nickel(0)-phosphorus ligand complexes as catalysts,
   b) adiponitrile, 2-methylglutaronitrile and nickel(0)-phosphorus ligand complex are removed from the hydrocyanation output, thereby obtaining an organic phase,
   c) the cis-2-pentenenitrile in the thus obtained organic phase comprising unsaturated C5 mononitriles is isomerized to 3-pentenenitriles with the aid of 1,4-diazabicyclo[2.2.2]octane as a catalyst, which has a higher boiling point at standard pressure than cis-2-pentenenitrile,
   wherein
   d) the organic phase which comprises essentially unsaturated C5 mononitriles and is obtained in c) is supplied to a distillation column K1, cis-2-pentenenitrile and cis- and trans-2-methyl-2-butenenitrile are removed from the distillation column K1 via the top, and 3-pentenenitrile and trans-2-pentenenitrile are removed from the distillation column K1 via the bottom and are recycled into the reaction step for hydrocyanation of 3-pentenenitriles,
   e) the top product from the distillation column K1 is fed to a distillation column K2, and trans-2-methyl-2-butenenitrile is removed and discharged as a bottom product of column K2,
   f) a top product from column K2 and 1,4-diazabicyclo[2.2.2]octane are supplied to a reactor R1, and the reaction product from the reactor R1 and the 1,4-diazabicyclo[2.2.2]octane are supplied to a distillation column K3, and
   g) a top product from distillation column K3 is recycled into the reactor R1 and a substream of the top product comprising cis-2-methyl-2-butenenitrile and cis-2-pentenenitrile is discharged, a mixture of cis-2-pentenenitrile, trans-3-pentenenitrile and trans-2-pentenenitrile from a side draw is recycled into the distillation column K1, and 1,4-diazabicyclo[2.2.2]octane and optionally high boilers are discharged as the bottom product.

5. The process for continuous isomerization of cis-2-pentenenitrile to 3-pentenenitriles according to claim 4, wherein the unsaturated C5 mononitriles comprise one or more of cis-3-pentenenitriles and trans-3-pentenenitriles, 4-pentenenitrile, trans-2-pentenenitrile, cis-2-methyl-2-butenenitrile, trans-2-methyl-2-butenenitrile, or 2-methyl-3-butenenitrile.

6. The process for continuous isomerization of cis-2-pentenenitrile to 3-pentenenitriles according to claim 4, wherein the isomerization of cis-2-pentenenitriles is performed in a reaction column.

\* \* \* \* \*